(12) United States Patent
Yamamori

(10) Patent No.: US 7,841,988 B2
(45) Date of Patent: Nov. 30, 2010

(54) NASAL MASK FOR CARBON DIOXIDE GAS MEASUREMENT

(75) Inventor: Shinji Yamamori, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 439 days.

(21) Appl. No.: 11/774,188

(22) Filed: Jul. 6, 2007

(65) Prior Publication Data

US 2008/0196715 A1 Aug. 21, 2008

(30) Foreign Application Priority Data

Feb. 16, 2007 (JP) .............................. 2007-035846

(51) Int. Cl.
*A61B 5/08* (2006.01)
*A62B 18/02* (2006.01)
*A62B 7/00* (2006.01)

(52) U.S. Cl. .................. 600/532; 600/529; 128/206.24; 128/206.21; 128/204.23

(58) Field of Classification Search ......... 600/529–543; 128/203.12, 204.22, 205.11, 205.24, 206.21, 128/206.28

See application file for complete search history.

(56) References Cited

U.S. PATENT DOCUMENTS

| | | | | |
|---|---|---|---|---|
| 5,046,491 A | * | 9/1991 | Derrick ................... | 128/200.24 |
| 5,400,781 A | * | 3/1995 | Davenport ............. | 128/206.28 |
| 5,474,060 A | * | 12/1995 | Evans ..................... | 128/204.22 |
| 5,857,460 A | * | 1/1999 | Popitz ................... | 128/206.21 |
| 6,017,315 A | * | 1/2000 | Starr et al. ................... | 600/538 |
| 6,273,087 B1 | * | 8/2001 | Boussignac et al. .... | 128/204.22 |
| 6,342,040 B1 | * | 1/2002 | Starr et al. ................... | 600/538 |
| 6,357,440 B1 | * | 3/2002 | Hansen et al. ......... | 128/206.19 |
| 6,402,698 B1 | * | 6/2002 | Mault .......................... | 600/532 |
| 6,406,435 B1 | * | 6/2002 | Mault .......................... | 600/532 |
| 6,478,736 B1 | * | 11/2002 | Mault .......................... | 600/300 |
| 6,544,192 B2 | * | 4/2003 | Starr et al. ................... | 600/538 |
| 6,565,517 B1 | * | 5/2003 | Rasmussen ................. | 600/529 |
| 6,599,252 B2 | * | 7/2003 | Starr .......................... | 600/532 |
| 6,612,306 B1 | * | 9/2003 | Mault .................... | 128/204.22 |
| 6,629,532 B2 | * | 10/2003 | Campbell, Sr. ......... | 128/207.11 |

(Continued)

FOREIGN PATENT DOCUMENTS

JP 2002-520104 A 7/2002

(Continued)

*Primary Examiner*—Charles A Marmor, II
*Assistant Examiner*—Navin Natnithithadha
(74) *Attorney, Agent, or Firm*—Sughrue Mion, PLLC

(57) ABSTRACT

A nasal mask is adapted to attached on a face of a subject so as to cover a nose of the subject. A shell has a contact edge adapted to be brought into close contact with the face of the subject, thereby forming a sealed space therein. An attachment portion is disposed in the shell and has an inner space. The attachment portion is configured to detachably engage with a sensor disposed outside the shell and operable to measure concentration of carbon dioxide gas expired from the nostrils. A guide member is disposed inside the shell and forming a passage adapted to introduce expired gas from the nostrils into the inner space. The shell is formed with an inlet adapted to introduce external gas into the sealed space. The expired gas is guarded by the guide member from the external gas introduced through the inlet. The attachment portion is formed with an outlet adapted to discharge the expired gas from the inner space to the sealed space.

7 Claims, 7 Drawing Sheets

U.S. PATENT DOCUMENTS

| | | | |
|---|---|---|---|
| 6,645,158 B2* | 11/2003 | Mault | 600/532 |
| 6,849,049 B2* | 2/2005 | Starr et al. | 600/538 |
| 7,004,168 B2 | 2/2006 | Mace et al. | |
| 7,089,932 B2* | 8/2006 | Dodds | 128/202.22 |
| 7,204,250 B1* | 4/2007 | Burton | 128/205.23 |
| 7,462,154 B2* | 12/2008 | Yamamori et al. | 600/532 |
| 7,568,483 B2* | 8/2009 | Scarberry et al. | 128/206.21 |
| 2002/0029004 A1* | 3/2002 | Starr et al. | 600/538 |
| 2002/0122746 A1 | 9/2002 | Yamamori et al. | |
| 2003/0130591 A1* | 7/2003 | Starr et al. | 600/538 |
| 2004/0163648 A1* | 8/2004 | Burton | 128/204.21 |
| 2006/0081248 A1* | 4/2006 | McDonald | 128/205.25 |
| 2006/0196510 A1* | 9/2006 | McDonald et al. | 128/206.21 |
| 2006/0201505 A1* | 9/2006 | Remmers et al. | 128/204.21 |
| 2006/0249160 A1* | 11/2006 | Scarberry et al. | 128/207.13 |
| 2008/0027344 A1* | 1/2008 | Terry | 600/532 |
| 2008/0092898 A1* | 4/2008 | Schneider et al. | 128/206.28 |
| 2008/0196715 A1* | 8/2008 | Yamamori | 128/203.12 |
| 2008/0319334 A1* | 12/2008 | Yamamori | 600/532 |
| 2009/0088657 A1* | 4/2009 | Yamamori et al. | 600/532 |

FOREIGN PATENT DOCUMENTS

| | | |
|---|---|---|
| JP | 2003-315264 A | 11/2003 |
| WO | 00/03243 A2 | 1/2000 |
| WO | 03/022329 A2 | 3/2003 |

* cited by examiner

NASAL MASK FOR CARBON DIOXIDE GAS MEASUREMENT

BACKGROUND

The present invention relates to a nasal mask adapted to be used in carbon dioxide gas measurement, and more particularly, used with an apparatus for a CPAP (Continuous Positive Airway Pressure) therapy or an NPPV (Noninvasive Positive Pressure Ventilation) therapy that is used for treatments for patients suffering from sleep apnea syndromes or respiratory failure.

In the treatments, a nasal mask is fixed to tightly contact an area around a nose for preventing leakage from a gap therebetween and pressure inside the nasal mask is increased by using gas such as oxygen or air that is transmitted from the apparatus described above. Although the object of the CPAP therapy or the NPPV therapy is to improve the ventilation state of patients, the enhancement of the concentration of carbon dioxide gas accumulated in the patients' bodies due to hypoventilation can be acquired quantitatively by simultaneously measuring carbon dioxide gas in the expired gas. To be more specific, there is a desirable value for the concentration of carbon dioxide gas, and a difference between an actual concentration of carbon dioxide gas and the desirable value can be recognized at a glance. In addition, an optimal level of the positive pressure or an optimal number of respirations in the NPPV therapy can be set in a simple manner by acquiring the concentration of carbon dioxide gas in the expired gas. Further, by continuously monitoring the concentration of carbon dioxide gas in the expired gas, it is possible to immediately detect accidents in connection with abnormalities of respiratory circuit of the patient, respiratory condition of the patient, and measurement equipments, and to notify the same to a medical staff.

Japanese Patent Publication No. 2003-315264A discloses a configuration for measuring carbon dioxide gas, in which the expired gas is guided to a sensor by inserting nasal tubes in nostrils. However, since a sensor body is positioned right below the nostrils, contaminations such as nasal discharge are adhered on the sensor body along with the nasal tubes, and whereby the precision of the measurement is lowered. Accordingly, the frequency of cleaning and sterilization of the sensor should be increased or the sensor should be replaced in a short period. In addition, when oxygen or air that has been humidified is supplied to the inside of the mask, the frequency of cleaning and sterilization of the sensor should be increased further more. In addition, when the carbon dioxide gas sensor is included inside the mask, a gap between a cable and the mask is formed to cause the occurrence of a leak, and the efficiency for generating a positive pressure is decreased, and in a worst case, the positive pressure cannot be generated.

U.S. Pat. No. 7,004,168B2 discloses a configuration that measures carbon dioxide gas by extracting the expired gas together with sending oxygen to the mask. However, in this structure, precise measurement of concentration of carbon dioxide gas cannot be performed since the expired gas and oxygen supplied from the outside are mixed inside the mask and the expired gas is diluted by the supplied oxygen. In addition, since the inside of the mask is opened to the air, it is difficult to maintain a positive pressure inside the mask even by sending oxygen or the like forcibly.

Japanese Patent Publication No. 2002-520104T discloses a configuration in which a carbon dioxide gas sensor is attached outside the mask. In this case, since an end of the sensor which is not attached to the mask is opened to the air, it is difficult to maintain a positive pressure inside the mask even by sending oxygen or the like forcibly.

SUMMARY

It Is therefore one advantageous aspect of the invention to provide a mask capable of measuring the precise concentration of carbon dioxide gas without allowing contamination caused by nasal discharge or humidified gas introduced into the mask from the outside to reach a sensor, and being adapted to forcibly send oxygen or the like inside the mask.

According to the invention, there is provided a nasal mask, adapted to attached on a face of a subject so as to cover a nose of the subject, comprising:

a shell, having a contact edge adapted to be brought into close contact with the face of the subject, thereby forming a sealed space therein;

an attachment portion, disposed in the shell and having an inner space, the attachment portion being configured to detachably engage with a sensor disposed outside the shell and operable to measure concentration of carbon dioxide gas expired from the nostrils; and a guide member, disposed inside the shell and forming a passage adapted to introduce expired gas from the nostrils into the inner space, wherein:

the shelf is formed with an inlet adapted to introduce external gas into the sealed space;

the expired gas is guarded by the guide member from the external gas introduced through the inlet; and the attachment portion is formed with an outlet adapted to discharge the expired gas from the inner space to the sealed space.

With this configuration, the expired gas is guided to the attachment portion without being diluted by the gas introduced from the inlet, and the concentration of carbon dioxide gas is detected by the sensor engaged with the attachment portion.

The guide member may be a tube member adapted to communicate the nostrils and the inner space.

The guide member may be a cup member integrally provided with the attachment portion and adapted to cover the nose. An inner space of the cup member may be communicated with the inner space of the attachment portion.

The shell may be formed with a recessed part adapted to receive the sensor, and the attachment portion is projected into the recessed part.

With this configuration, it is possible to cause the sensor to engage with the attachment portion securely.

The attachment portion may be monolithically formed with the shell.

The attachment portion may be detachably fitted with an aperture formed in the recessed part.

DETAILED DESCRIPTION OF THE EXEMPLIFIED EMBODIMENTS

Figure 1:
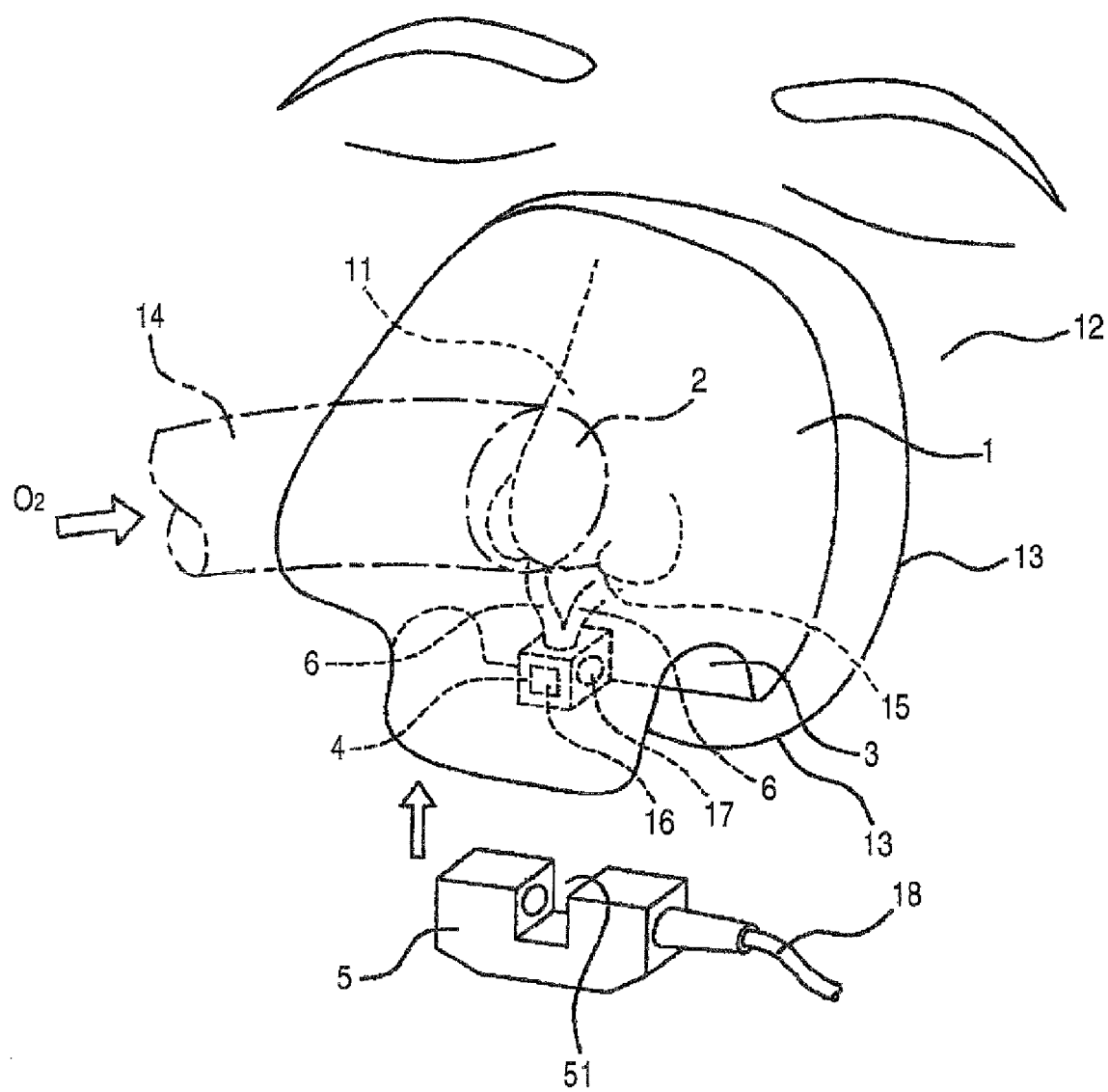
FIG. 1 is a perspective view showing a nasal mask for measuring carbon dioxide gas according to a first embodiment of the invention.

Embodiments of the invention will be described below in detail with reference to the accompanying drawings. Similar components will be designated by the same reference numerals and repetitive explanations for those will be omitted.

A first embodiment of the invention will be described with reference to FIGS. 1 through 3. In this embodiment, a mask for measuring carbon dioxide gas comprises a nasal mask shell 1 made of vinyl chloride and having a contact edge 13 that tightly contacts a human face 12 so as to cover a nose 11 and forms a sealed space therein. An inlet 2 for introducing oxygen or air from the outside to a space covered by the nasal mask shell 1 through an air hose 14 is formed in the approximate center of a front side of the nasal mask shell 1.

The nasal mask shell 1 is formed to protrude on the whole toward a front side from the human fare 12 for covering the nose 11. A part of the nasal mask shell 1 adapted to be placed below the nose 11 is formed with a groove portion 3 having a shape recessed toward the inside from the outside thereof. In the longitudinal center of the groove portion 3, there is provided a cube-shaped attachment portion 4, the inside of which is formed as a space so as to protrude from the ceiling side of the groove portion 3. The groove portion 3 may be formed in the shape of a hole.

The attachment portion 4 is formed in a part of the nasal mask shell 1 and is configured to be positioned right below a nostrils 15 in a state that the nasal mask shell 1 is worn. The attachment portion 4 is used for introducing expired gas from the nostrils 15, and has an expired gas outlet 16 on the front side thereof. A carbon dioxide gas sensor 5 is attached to the attachment portion 4 in a detachable manner. In the attachment portion 4, there are provided transparent windows 17 facing the groove portion 3 in the longitudinal direction thereof. The windows 17 can be seen when viewed from both ends of the groove portion 3 toward the center portion thereof. A peripheral portion of the expired gas outlet 16 is formed integrally with a wall face of the groove portion 3 or is configured to be bonded to the wall face of the groove portion 3. When the peripheral portion of the expired gas outlet 16 is configured to be bonded to the wall face of the groove portion 3, an opening is formed on the wall face of the groove portion 3 in a position corresponding to the expired gas outlet 16. A wall portion of the attachment portion 4 facing the expired gas outlet 16 has a same structure as the peripheral portion of the expired gas outlet 16.

On the upper side of the attachment portion 4, there is provided an Y-shaped nasal tube 6 for acquiring a passage that is used for guiding the expired gas, which is introduced to the inside of the attachment portion 4 from the nostrils 15, to the attachment portion 4 in the nasal mask shell 1 without allowing the expired gas to be diluted by gas coming from the inlet 2. The attachment portion 4 is fitted to an opening that is formed in the longitudinal center of the ceiling of the groove portion 3 of the nasal mask shell 1. A fitting portion is sealed by a packing.

The carbon dioxide gas sensor 5 has a same structure as that disclosed in FIG. 2(b) of Japanese Patent Publication No. 2003-315264A described above. Specifically, the attachment portion 4 is inserted into a recessed portion 51 of the carbon dioxide gas sensor 5 and a lead wire 18 is connected to a light receiving element and a light emitting element. However, the carbon dioxide gas sensor 5 may has a structure in which the attachment portion 4 is fitted to both sides of the carbon dioxide gas sensor 5 as shown in FIG. 15 of Japanese Patent Publication No. 2003-315264A.

One of the carbon dioxide gas sensor 5 and the attachment portion 4, for example, is provided with a hook, and the other of the carbon dioxide gas sensor 5 and the attachment portion 4 is provided with a fitting hole formed in a position corresponding to the hook, and the carbon dioxide gas sensor 5 and the attachment portion 4 are combined using the hook and the fitting hole. The nasal mask shell 1 is fixed to a head or an ear using a band that is not shown in the figure.

With the above configuration, since the expired gas reaches the attachment portion 4 through the nasal tube 6 and discharges from the expired gas outlet 16 into the inside of the nasal mask shell 1, a precise measurement of concentration of carbon dioxide gas can be performed with hardly being influenced by oxygen or the like that has reached the inlet 2. In addition, since the nasal mask shell 1 tightly contacts the human face 12 using the contact edge 13, the oxygen or the like arriving at the inlet 2 can be used for generating a positive pressure, and accordingly, the nasal mask can be used in an apparatus for a CPAP therapy or an NPPV therapy that is used for treatments for patients suffering from sleep apnea syndromes or respiratory failure.

In addition, by replacing the attachment portion 4 and the nasal tube 6 of the carbon dioxide gas measuring nasal mask after use or replacing components other than the carbon dioxide gas sensor 5, a cleaning operation for contaminations is not required, and whereby a measuring operation or the like can progress efficiently.

Figure 4:
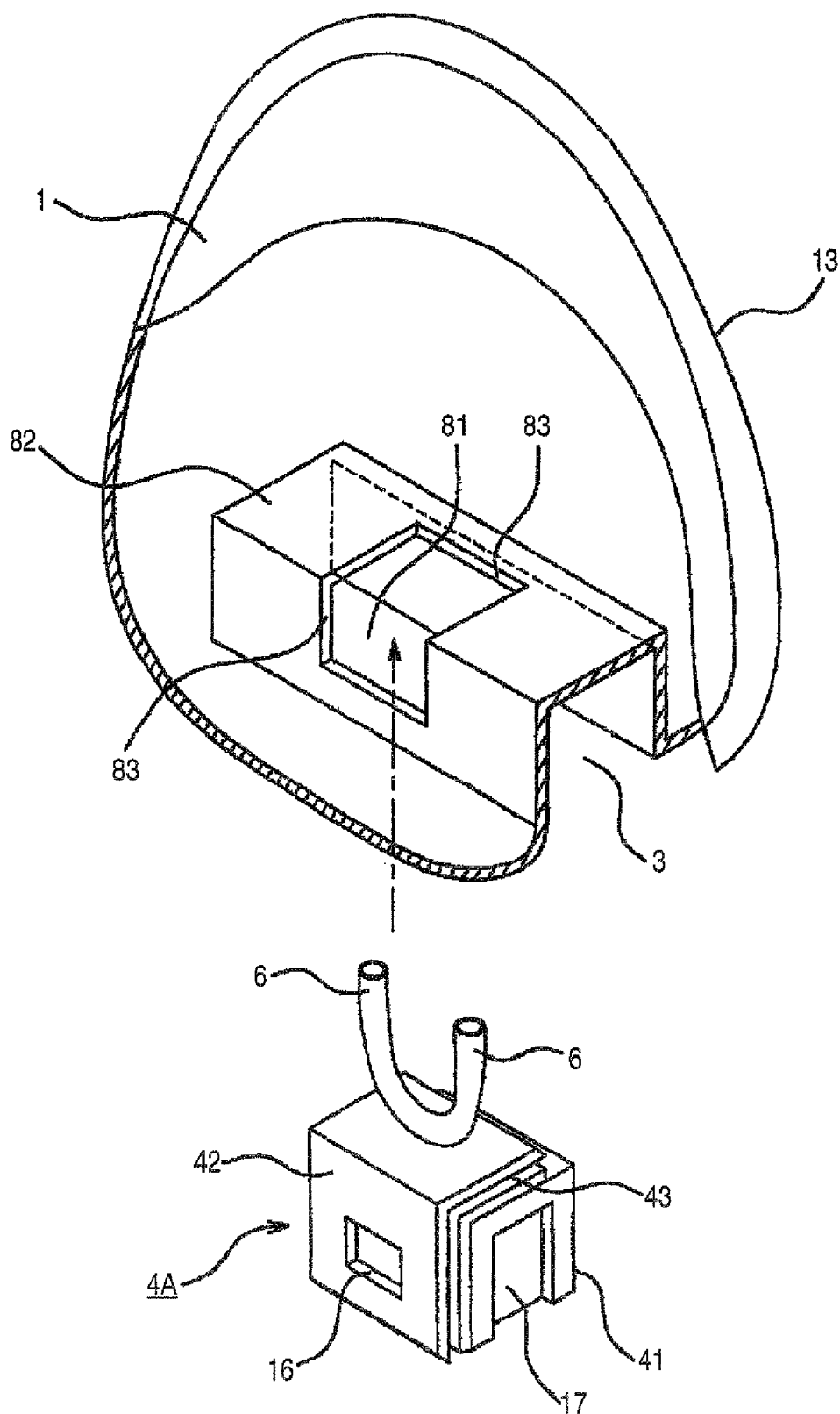
FIG. 4 is a perspective view showing a modified example of the nasal mask of FIG. 1.

A modified example of the mask of the first embodiment will be described with reference to FIGS. 4 and 5. In this example the groove portion 3 is formed with an opening portion 81 at the longitudinal center thereof. The opening portion 81 has such a shape that a rectangular portion is cut away from a ceiling portion of a wall portion 82 forming the groove portion 3 to a front portion of the wall portion 82.

An attachment portion 4A is fitted to the opening portion 81. The attachment portion 4A includes an approximate cube-shaped hollow case 41 and a packing 42 that is a rubber casting product bonded to the case 41. A nasal tube 6 is attached to a top board of the cube. The nasal tube 6 is connected to an inner space of the case 41. On both sides of the case 41, windows 17 are provided.

In the front center of the packing 42 and the case 41, there is formed an expired gas outlet 16 which is connected to the inner space of the case 41. In the side of the packing 42, there are formed a groove 43 contacting an edge 83 of the opening portion 81 and bank portions 44 and 45 of the groove 43. The bank portions 44 and 45 extrude outside from the groove 43, and in a state that the edge 83 of the opening portion contacts the groove 43, the bank portions 44 and 45 sandwiches the wall portion 82 therebetween, whereby sealing the opening portion 81.

Figure 5:
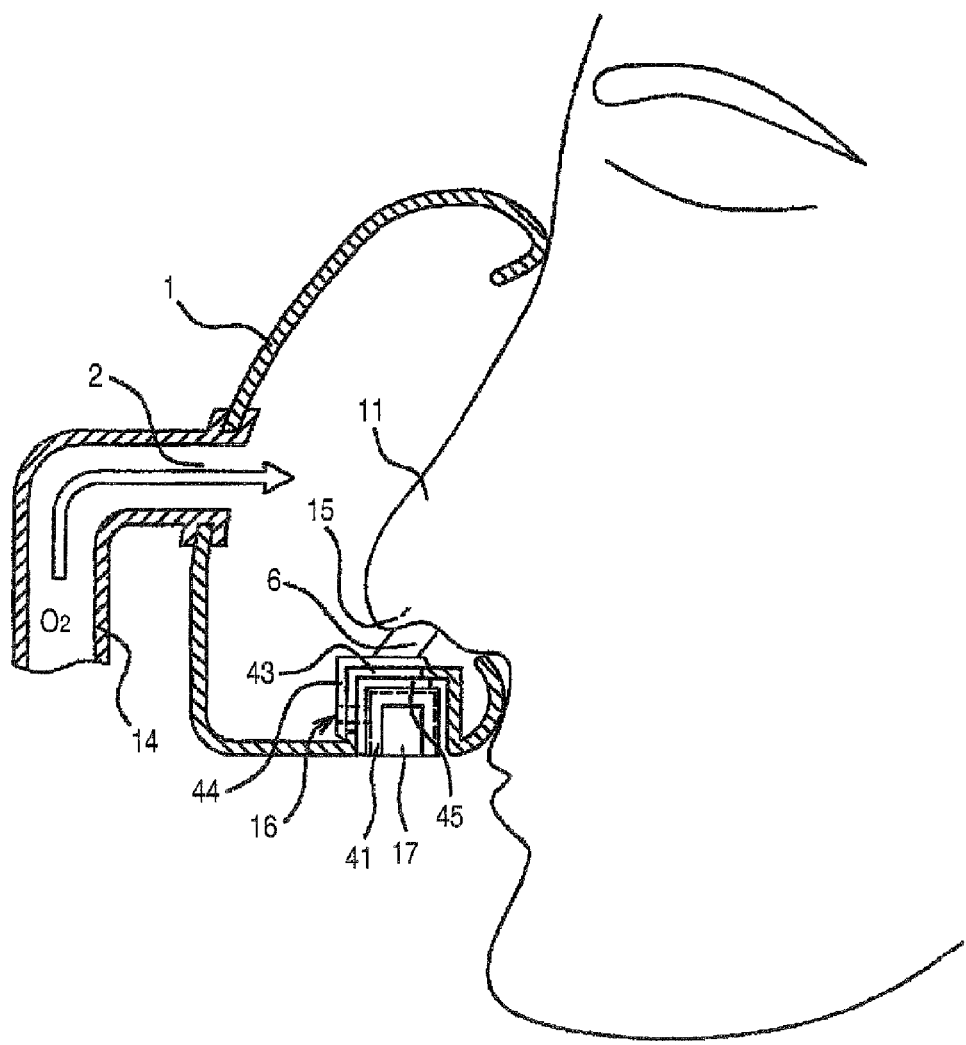
FIG. 5 is a side section view of the nasal mask of FIG. 4.

In a state that the attachment portion 4A is attached to the opening portion 81 as shown in FIG. 5, the expired gas reaches the inner space of the case 41 from the nasal tube 6 and is sent from the expired gas outlet 16 to the inside of the nasal mask shell 1. Oxygen or the like reaches the nasal mask shell 1 from the air hose 14 through the inlet 2.

Figure 2:
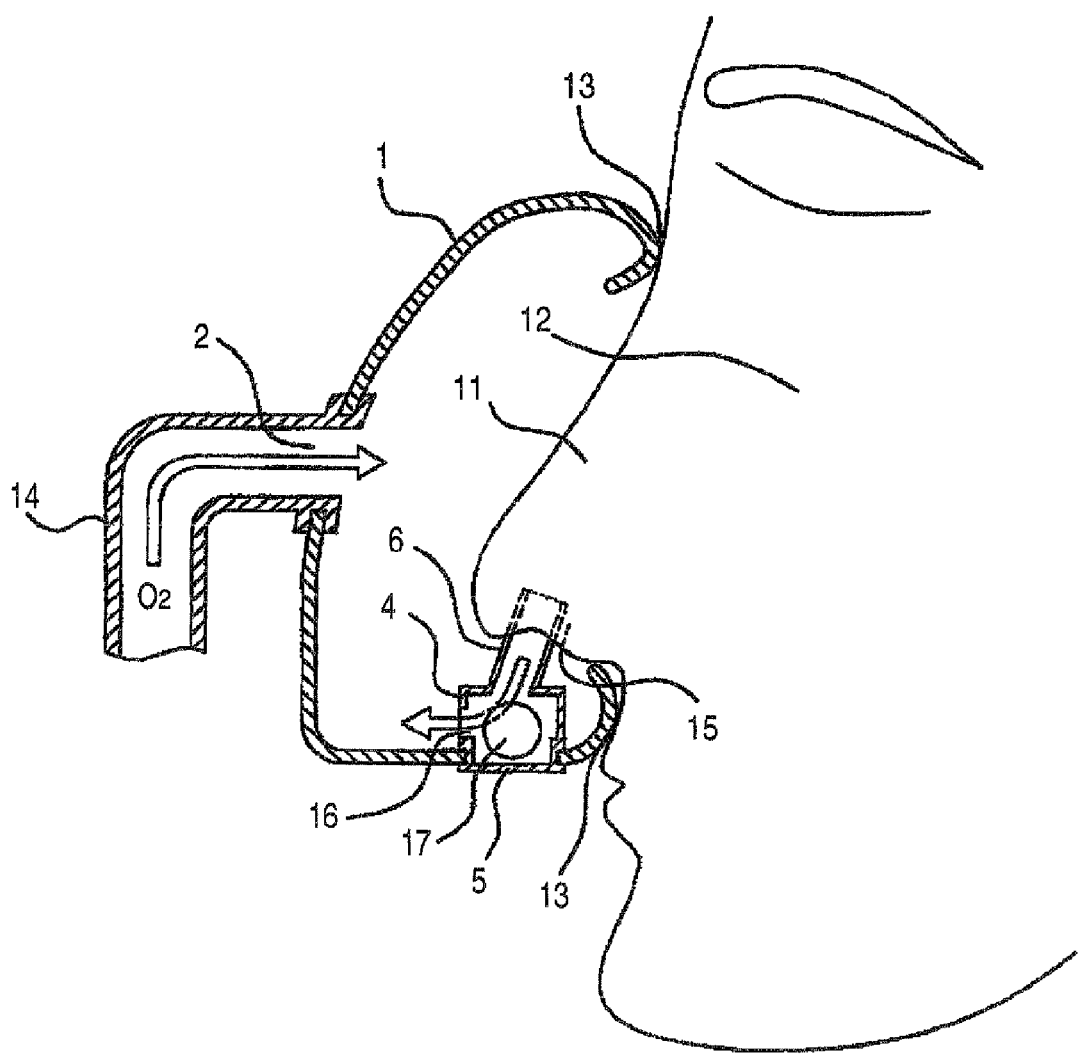
FIG. 2 is a side section view of the nasal mask of FIG. 1.
Figure 3:
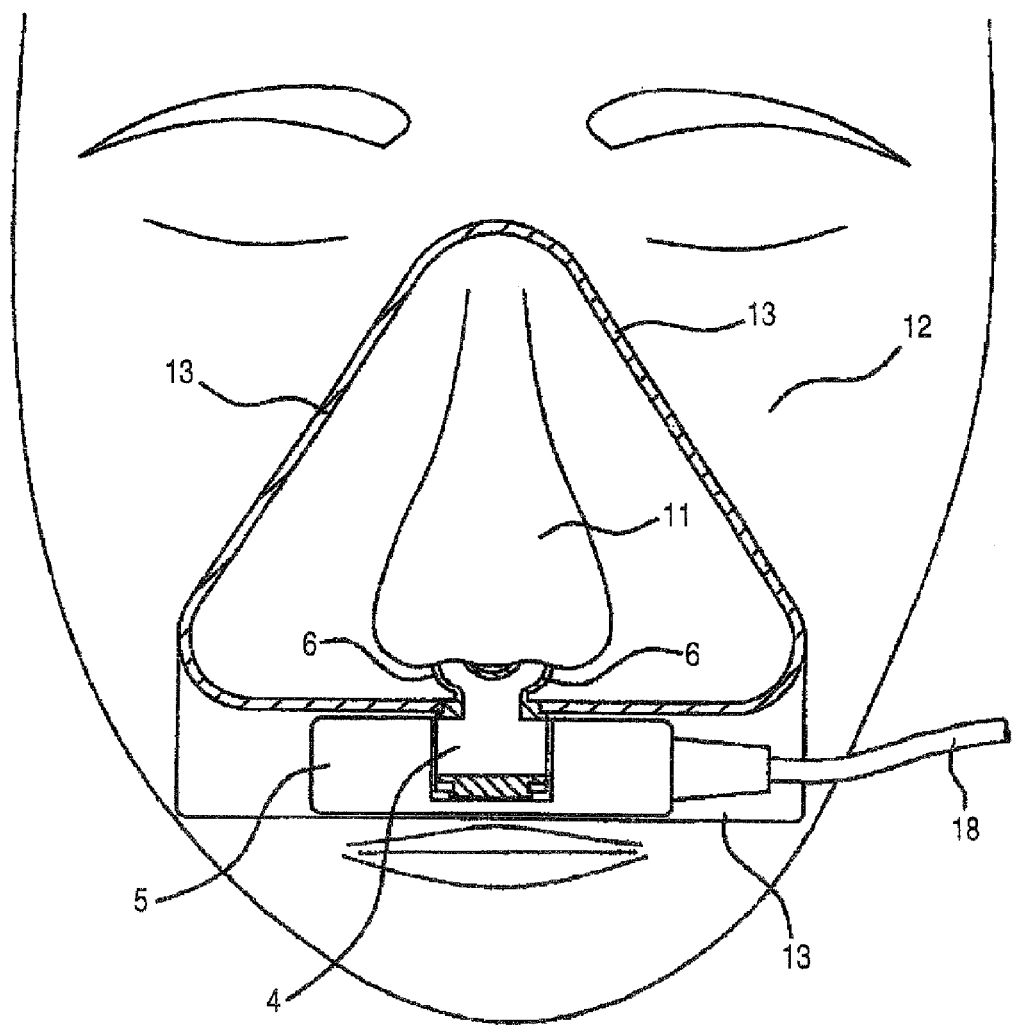
FIG. 3 is a front section view of the nasal mask of FIG. 1.

With the above configuration, the carbon dioxide gas sensor 5 is attached to the attachment portion 4A, so that the mask can be used as well as the mask shown in FIGS. 1 to 3, and the same advantages can be attained.

Figure 6:
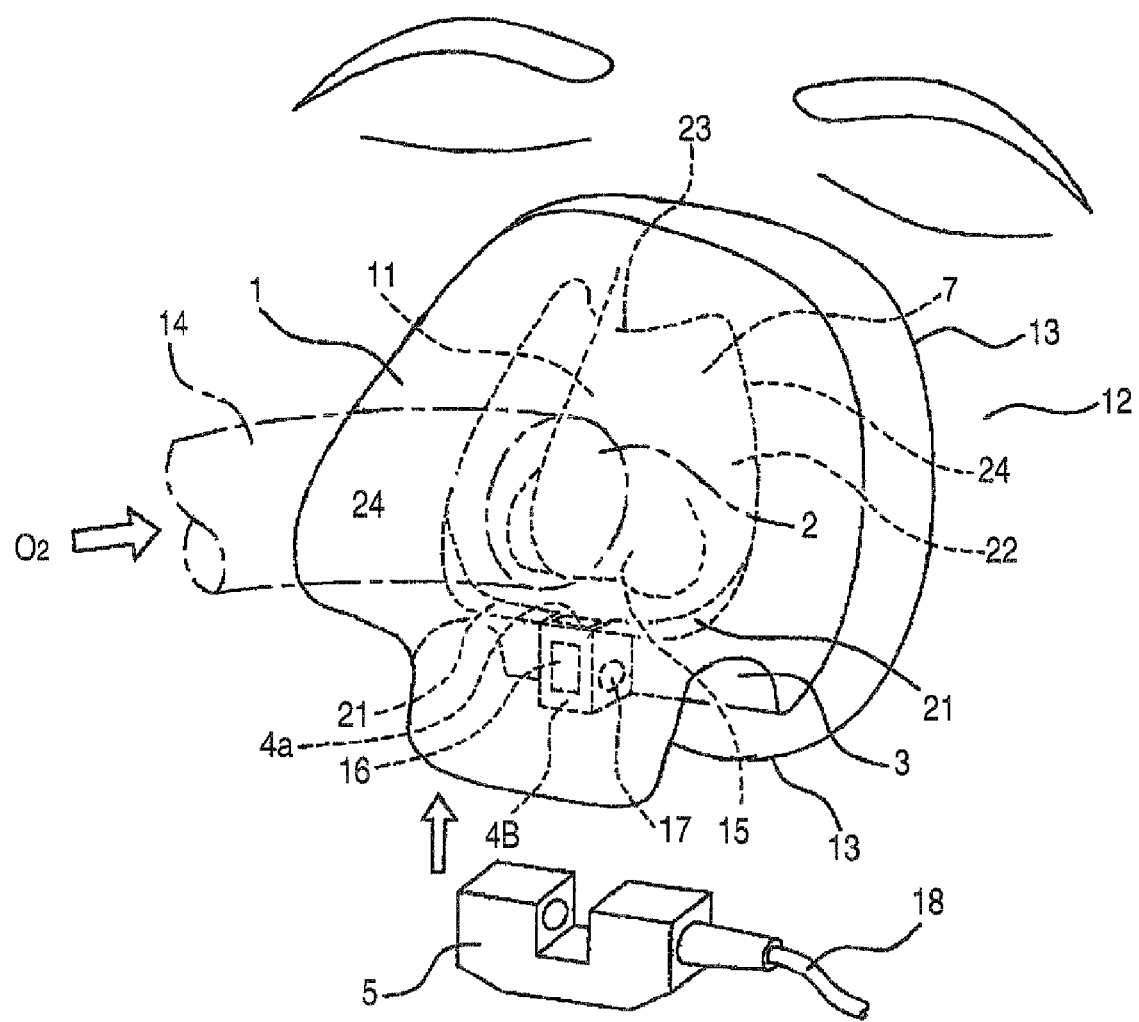
FIG. 6 is a perspective view showing a nasal mask for measuring carbon dioxide gas according to a second embodiment of the invention.
Figure 7:
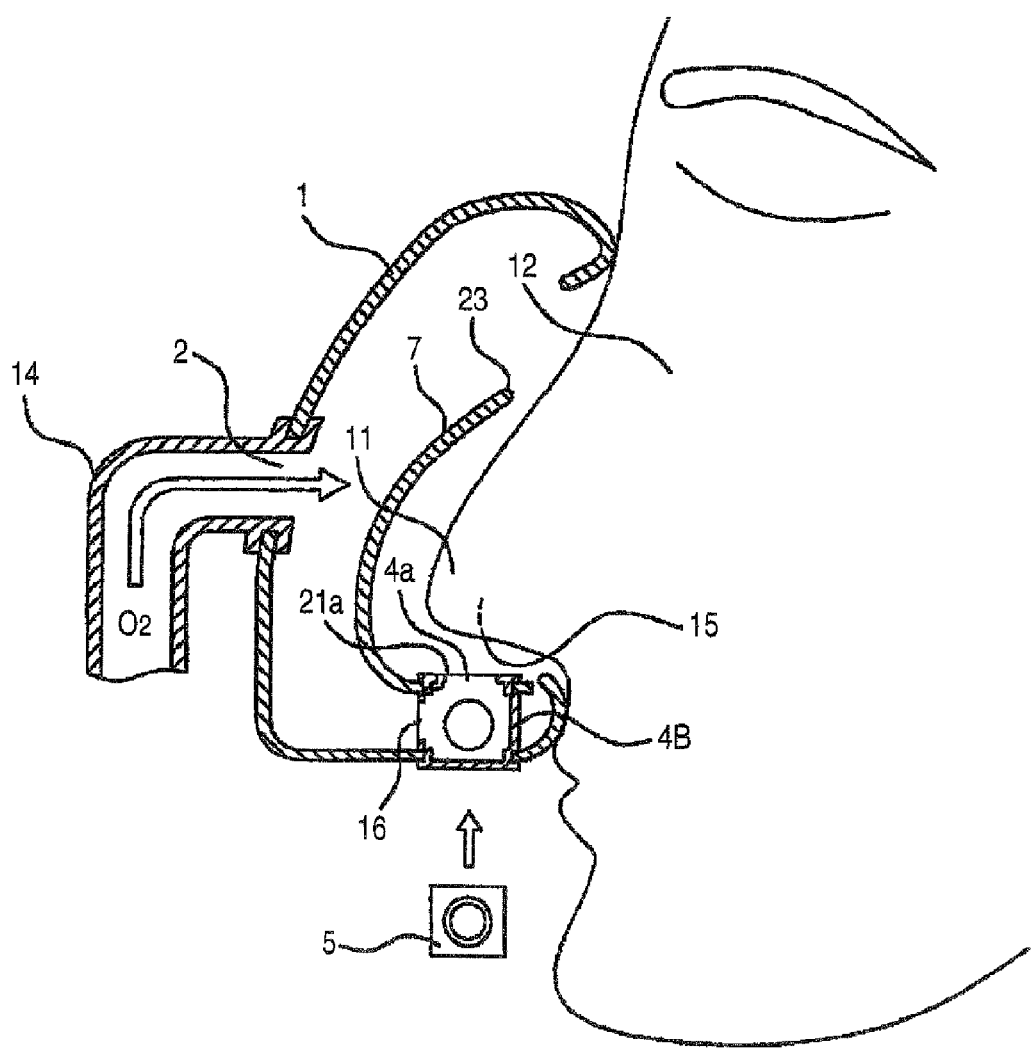
FIG. 7 is a side section view of the nasal mask of FIG. 6.

Next, a second embodiment of the invention will be described with reference to FIGS. 6 and 7. In this embodiment, a nasal cup 7 that is disposed in the inside of the nasal mask shell 1 and has a shape for covering the nose 11 and guiding the expired gas from the nostrils to the attachment portion 4B is provided, instead of the nasal tube 6 provided on the upper side of the attachment portion 4B.

The nasal cup 7 has a protruded shape that is like a miniaturized nasal mask shelf 1. The nasal cup 7 includes a bottom portion 21 that is configured to be positioned below the nostrils 15 in a state that the nasal mask shell 1 is worn and a body portion 22 that covers an upper portion of the nose 11. In a state that the mask is worn, an upper portion of the body portion 22 is configured such that a curved portion 23 is formed so as not to contact the human face 12 and a gap is formed between the curved portion 23 and the human face 12. Right below the nostrils 15 of the bottom portion 21, an attachment hole 21a for fixing the bottom portion 21 to the attachment portion 4B is provided. In addition, on the top wall of the attachment portion 4B, an inlet 4a for introducing the expired gas to the inside of the attachment portion 4B is provided.

A periphery portion 24 of the nasal cup 7 other than the curved portion 23 is configured to contact the human face 12 in the vicinity of the nose 11. The periphery portion 24 of the nasal cup 7 other than the curved portion 23 and the contact edge 13 of the nasal mask shell 1 may be connected to each other smoothly with a connection face to form a dual structure in a position other than the curved portion 23. Alternatively, the connection face may not be provided. In any case, gas such as oxygen coming from the inlet 2 does not directly reach the nostrils 15 due to the nasal cup 7 and is basically sent to the nostrils 15 through the gap between the curved portion 23 and the human face 12.

In this embodiment, since the expired gas reaches the attachment portion 4B from the nostrils 15 through the nasal cup 7 and the inlet 4a, and flows to the inside of the nasal mask shell 1 from the expired gas outlet 16, it is possible to measure the concentration of carbon dioxide gas appropriately by using the carbon dioxide gas sensor 5 attached to the attachment portion 4B without being influenced by the oxygen or the like supplied through the inlet 2. In addition, the mask is configured such that most of the oxygen or the like that has been supplied to the inlet 2 can be sent to the nostrils 15 through the gap formed between the curved portion 23 and the human face 12 (some through the expired gas outlet 16) with a positive pressure. Since the supplied oxygen or the like can be used for the positive pressure, the nasal mask can be used in an apparatus for a CPAP therapy or an NPPV therapy that is used for treatments for patients suffering from sleep apnea syndromes or respiratory failure.

Although only some exemplary embodiments of the invention have been described in detail above, those skilled in the art will readily appreciated that many modifications are possible in the exemplary embodiments without materially departing from the novel teachings and advantages of the invention. Accordingly, all such modifications are intended to be included within the scope of the invention.

The disclosure of Japanese Patent Application No. 2007-35846 filed Feb. 18, 2007 including specification, drawings and claims are incorporated herein by reference in their entirety.

What is claimed is:

1. A nasal mask, adapted to be attached to a face of a subject so as to cover a nose of the subject, comprising:
   a shell, having a contact edge adapted to be brought into close contact with the face of the subject, thereby forming a sealed space therein;
   an attachment portion, disposed in the shell and having an inner space, the attachment portion being configured to detachably engage with a sensor disposed outside the shell and operable to measure concentration of carbon dioxide gas expired from the nostrils; and
   a guide member, disposed inside the shell and forming a passage adapted to introduce expired gas from nostrils into the inner space, wherein:
   the shell is formed with an inlet adapted to introduce external gas into the sealed space;
   the expired gas is guarded by the guide member from the external gas introduced through the inlet; and
   the attachment portion is formed with an outlet adapted to discharge the expired gas from the inner space to the sealed space.

2. The nasal mask as set forth in claim 1, wherein:
   the guide member is a nasal tube member adapted to be placed within the nostrils so as to communicate the nostrils and the inner space.

3. The nasal mask as set forth in claim 1, wherein:
   the guide member is a cup member integrally provided with the attachment portion and adapted to cover the nose; and
   an inner space of the cup member is communicated with the inner space of the attachment portion.

4. The nasal mask as set forth in claim 1, wherein:
   the shell is formed with a recessed part adapted to receive the sensor, and the attachment potion is projected into the recessed part.

5. The nasal mask as set forth in claim 4, wherein:
   the attachment portion is monolithically formed with the shell.

6. The nasal mask as set forth in claim 4, wherein:
   the attachment portion is detachably fitted with an aperture formed in the recessed part.

7. The nasal mask as set forth in claim 1, wherein:
   the nasal mask is configured such that the expired gas travels first from the nostrils and then through the inner space and then to the sealed space.

* * * * *